(12) United States Patent
Pugh et al.

(10) Patent No.: US 9,282,796 B2
(45) Date of Patent: Mar. 15, 2016

(54) UV RADIATION CONTROL FOR DISINFECTING OF OPHTHALMIC LENSES

(75) Inventors: Randall B. Pugh, Jacksonville, FL (US); Edward R. Kemick, Jacksonville, FL (US); Karson S. Putt, Jacksonville, FL (US); James Daniel Riall, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 5 days.

(21) Appl. No.: 13/359,044

(22) Filed: Jan. 26, 2012

(65) Prior Publication Data

US 2012/0138819 A1    Jun. 7, 2012

Related U.S. Application Data

(63) Continuation-in-part of application No. 12/961,616, filed on Dec. 7, 2010.

(60) Provisional application No. 61/346,162, filed on May 19, 2010.

(51) Int. Cl.
   *A61L 12/00* (2006.01)
   *A45C 11/00* (2006.01)
   *A61L 12/06* (2006.01)

(52) U.S. Cl.
   CPC ............. *A45C 11/005* (2013.01); *A61L 12/063* (2013.01)

(58) Field of Classification Search
   USPC .................................................... 250/445.11
   See application file for complete search history.

(56) References Cited

U.S. PATENT DOCUMENTS

| | | | |
|---|---|---|---|
| 3,621,855 A | | 11/1971 | Rabinowitz |
| 3,852,032 A | | 12/1974 | Urbach |
| 3,978,341 A | | 8/1976 | Hoell |
| 4,063,890 A | | 12/1977 | Baron |
| 4,412,834 A | | 11/1983 | Kulin |
| 4,529,868 A | * | 7/1985 | Bowen ...................... H05B 3/14 219/386 |
| 4,545,479 A | | 10/1985 | Figari |
| 4,735,223 A | * | 4/1988 | Ituarte ................... A61L 12/026 134/184 |
| 4,868,397 A | * | 9/1989 | Tittel ........................ 250/455.11 |

(Continued)

FOREIGN PATENT DOCUMENTS

| | | |
|---|---|---|
| CN | 101401949 A | 4/2009 |
| DE | 29509210 U1 | 10/1995 |

(Continued)

OTHER PUBLICATIONS

William A. Rutala, David J. Weber, and the Healthcare Infection Control Practices Advisory Committee, "Guideline for Disinfection and Sterilization in Healthcare Facilities", Center for Disease Control, 2008.*

(Continued)

*Primary Examiner* — Phillip A Johnston

(57) ABSTRACT

The present invention provides for a disinfecting radiation base with a radiation source for providing disinfecting radiation to a storage case for an ophthalmic lens, such as a contact lens. The disinfecting radiation base includes a diffusing material is molded into a shape or geometry that is capable of providing disinfecting radiation to all regions of the lens being disinfected in uniform intensity and contrast. The disinfecting radiation base may also include a processor and digital memory for automated functions associated with the base.

32 Claims, 14 Drawing Sheets

(56) References Cited

U.S. PATENT DOCUMENTS

| | | | |
|---|---|---|---|
| 5,120,499 A * | 6/1992 | Baron | A61L 12/026 250/455.11 |
| 5,144,144 A | 9/1992 | Borovsky | |
| 5,439,642 A | 8/1995 | Hagmann | |
| 5,440,458 A * | 8/1995 | Volk | F21V 33/0068 206/5.1 |
| 5,618,492 A | 4/1997 | Auten | |
| 6,030,554 A | 2/2000 | Ichihara | |
| 6,461,568 B1 * | 10/2002 | Eckhardt | 422/24 |
| 6,592,816 B1 | 7/2003 | Ebel | |
| 6,790,409 B1 | 9/2004 | Nakamura | |
| 7,169,037 B2 * | 1/2007 | Lin | 454/191 |
| 7,217,936 B2 | 5/2007 | Ressler | |
| 7,879,288 B2 | 2/2011 | Brown-Skrobot | |
| 8,277,741 B2 * | 10/2012 | McCabe | A61L 2/10 422/105 |
| 2004/0210123 A1 * | 10/2004 | Davidson | 600/398 |
| 2004/0234569 A1 | 11/2004 | Nakada | |
| 2005/0013729 A1 | 1/2005 | Brown-Skrobot | |
| 2005/0028848 A1 | 2/2005 | Lai | |
| 2005/0079096 A1 * | 4/2005 | Brown-Skrobot et al. | 422/24 |
| 2005/0173652 A1 | 8/2005 | Ressler | |
| 2007/0104611 A1 | 5/2007 | Marmo | |
| 2007/0206377 A1 * | 9/2007 | Borup | A45C 11/005 362/156 |
| 2008/0260601 A1 * | 10/2008 | Lyon | 422/186.3 |
| 2009/0086160 A1 | 4/2009 | Enns | |
| 2009/0096351 A1 * | 4/2009 | Hampden-smith et al. | 313/504 |
| 2009/0256085 A1 | 10/2009 | Thiruppathi | |
| 2009/0274576 A1 | 11/2009 | Ressler | |
| 2010/0266445 A1 | 10/2010 | Campagna | |
| 2010/0279124 A1 | 11/2010 | Scherer | |
| 2010/0320405 A1 | 12/2010 | Gardner, III | |
| 2011/0284773 A1 | 11/2011 | Pugh et al. | |
| 2012/0138819 A1 | 6/2012 | Pugh et al. | |

FOREIGN PATENT DOCUMENTS

| | | |
|---|---|---|
| EP | 1038536 A2 | 9/2000 |
| EP | 2067491 A | 6/2009 |
| FR | 2599255 A1 | 12/1987 |
| GB | 1453372 A | 10/1976 |
| JP | 5628763 A | 3/1981 |
| JP | 394758 | 4/1991 |
| JP | 4263213 A | 9/1992 |
| JP | 3131738 A | 2/1993 |
| JP | 7504758 A | 8/1993 |
| JP | 3100828 B | 8/1995 |
| JP | 07265394 A | 10/1995 |
| JP | 866678 | 12/1996 |
| JP | 2000507140 A | 10/1997 |
| JP | 2002126050 A | 5/2002 |
| JP | 2003093481 A | 4/2003 |
| JP | 2004159676 A | 6/2004 |
| JP | 2004275335 A | 10/2004 |
| JP | 2000245815 A | 1/2005 |
| JP | 2001066422 B | 12/2005 |
| KR | 20010092892 A | 10/2001 |
| KR | 20040071084 B | 8/2004 |
| KR | 2003095377 A | 4/2005 |
| KR | 100586927 B | 6/2006 |
| KR | 20070050328 | 5/2007 |
| KR | 20070050328 A | 5/2007 |
| RU | 57423 U | 10/2006 |
| RU | 69323 U | 10/2007 |
| TW | 202793 | 3/1981 |
| TW | M256699 | 4/1993 |
| TW | M319760 U | 5/1996 |
| TW | M367032 A | 10/2009 |
| WO | WO 9805438 A | 2/1998 |
| WO | WO 9938540 A | 8/1999 |
| WO | WO 2005/077076 A | 8/2005 |
| WO | WO 2006105180 A | 10/2006 |

OTHER PUBLICATIONS

PCT International Search Report, dated May 7, 2013, for PCT Int'l Appln. No. PCT/US2013/023010.

International Search Report for corresponding Application No. PCT/US2011/036836 mailed Aug. 3, 2011.

International Search Report for corresponding Application No. PCT/US2011/036832 mailed Aug. 3, 2011.

International Search Report for corresponding Application No. PCT/US2011/036826 mailed Aug. 3, 2011.

Harris, M.G., et al. "Ultraviolet Disinfection of Contact Lenses." *Optometry and Vision Science*, Oct. 1993;70(10): 839-42. Print.

Admoni, M.M., et al. "Disinfection Efficacy in an Integrated Ultraviolet Light Contact Lens Care System." *CLAO J*. Oct. 1994; 20(4): 246-8. Print.

Dolman, P.J., et al. "Contact Lens Disinfection by Ultraviolet Light." *American Journal of Ophthalmology*, Dec. 15, 1989;108(6):665-9.

"UV Kills These Bugs", *Review of Optometry*. Dec. 15, 1999 vol. 136 i12 p. 62.

"Device Cleans, Disinfects Soft Contact Lenses in 15 Minutes." *Ophthalmology Times*., Apr. 15, 2004 vol. 29 i8 p. 66.

* cited by examiner

UV RADIATION CONTROL FOR DISINFECTING OF OPHTHALMIC LENSES

RELATED APPLICATIONS

This application is a continuation-in-part of U.S. patent application Ser. No. 12/961,616 which was filed on Dec. 7, 2010 and entitled "OPHTHALMIC LENS DISINFECTING BASE," which claims the priority of U.S. Patent Application Ser. No. 61/346,162, filed on May 19, 2010 and entitled "OPHTHALMIC LENS DISINFECTING BASE," the contents of which are relied upon and incorporated by reference.

FIELD OF USE

This invention describes a case for storing an ophthalmic lens and, more specifically, in some embodiments, a base for receiving a case with disinfecting functionality while storing an ophthalmic lens such as a contact lens.

BACKGROUND

It is well known that contact lenses can be used to improve vision. Various contact lenses have been commercially produced for many years. Early designs of contact lenses were fashioned from hard materials. Although these lenses are still currently used in some applications, they are not suitable for all patients due to their poor comfort and relatively low permeability to oxygen. Later developments in the field gave rise to soft contact lenses, based upon hydrogels.

Hydrogel contact lenses are very popular today. These lenses are often more comfortable to wear than contact lenses made of hard materials. Many hydrogel contact lenses may be worn for more than one day. However, a build-up of microbial life and bacteria on the lenses generally makes it desirable to periodically remove the lenses and disinfect them.

Disinfection of contact lenses traditionally entails placing the contact lens in a container or case and subjecting the contact lens to a chemical disinfectant. However, chemical disinfectants are not always as efficacious as may be desired.

Furthermore, maintaining a clean environment during handling of a contact lens is generally considered essential to good ophthalmic health. One aspect of cleanliness that is often not adequately considered is a clean exterior of a contact lens case. Even if a contact lens handler conscientiously engages in hand-washing and proper use of lens solutions, the efficacy of such practices is limited if pathogens, such as bacteria and fungi may be present on the exterior of a contact lens case used to store the contact lenses.

As a result, from time to time, a contact lens with a bacterium, mold, fungus or other type of adverse life form is reinserted into a user's eye with the result being a diseased eye. In addition, most effective disinfecting solutions tend to be expensive and add to the total cost of using contact lenses for vision correction or cosmetic enhancement. New methods and approaches are therefore needed to disinfect contact lenses.

SUMMARY

Accordingly, the present invention includes a base for an ophthalmic lens storage case for storing reusable contact lenses and disinfecting the lenses during the storage. The lens storage case is capable of receiving disinfecting radiation in a wavelength and intensity suitable to kill unwanted bacteria, viruses, molds, fungi and the like on a contact lens. The base is capable of providing controlled disinfecting radiation in one or more wavelengths, and intensities, in durations suitable to kill the unwanted bacteria, viruses, molds, fungi and the like on a contact lens.

Various embodiments can include one or more radiation diffusing material types to control the disinfecting radiation intensity, wavelength, direction, contrast, and diffusion. For example, where the diffusing material is a fluoropolymer, such as, florinated ethelene propylene "FEP".

In addition in some embodiments, specific shape and geometries may be used to vary the intensity of the radiation delivered to the contact lens and to distribute the radiation across all areas of the contact lens in an even manner.

In another aspect, in some embodiments, a disinfecting radiation base includes one or more reflective surfaces, such as a mirror, for reflecting disinfecting radiation towards an ophthalmic lens stored in a storage case mounted in the disinfecting radiation base.

In yet another aspect, in some embodiments, a disinfecting base can additionally include a mechanism to measure and control the amount of UV dose delivered to specifically target the amount of disinfectant required for specific organisms.

Lastly, in some embodiments, the base provides vibrational frequency mechanically sufficient to effectively dislocate expired microbials and provide increased exposure of unexpired microbials to life extinguishing radiation.

DETAILED DESCRIPTION OF THE INVENTION

The present invention includes methods and apparatus for disinfecting an ophthalmic lens. In addition, the present invention includes a storage case for holding an ophthalmic lens while it is disinfected with disinfecting radiation.

In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

GLOSSARY

In this description and claims directed to the presented invention, various terms may be used for which the following definitions will apply:

Diffusing Material: as used herein refers to a material that is capable of diffusing disinfecting radiation due to its composition or with the use of a coating while not significantly degrading from exposure to the disinfecting radiation, wherein the diffusing material is at least partially transmissive to the disinfecting radiation. For example, the diffusing material may include a fluoropolymer such as fluorinated ethylene propylene (FEP) material or coating.

Disinfecting Radiation: as used herein refers to a frequency and intensity of radiation sufficient to diminish the life expectancy of a life form receiving a Disinfecting Radiation Dose.

Disinfecting Radiation Dose: as used herein refers to an amount of radiation to reduce an amount of life by at least two logs on a logarithmic scale and preferably three logs or more, wherein life includes at least bacteria, viruses, molds and fungi.

Lens: refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses made from silicone elastomers or hydrogels, which include but are not limited to silicone hydrogels, and fluorohydrogels.

Figure 1:
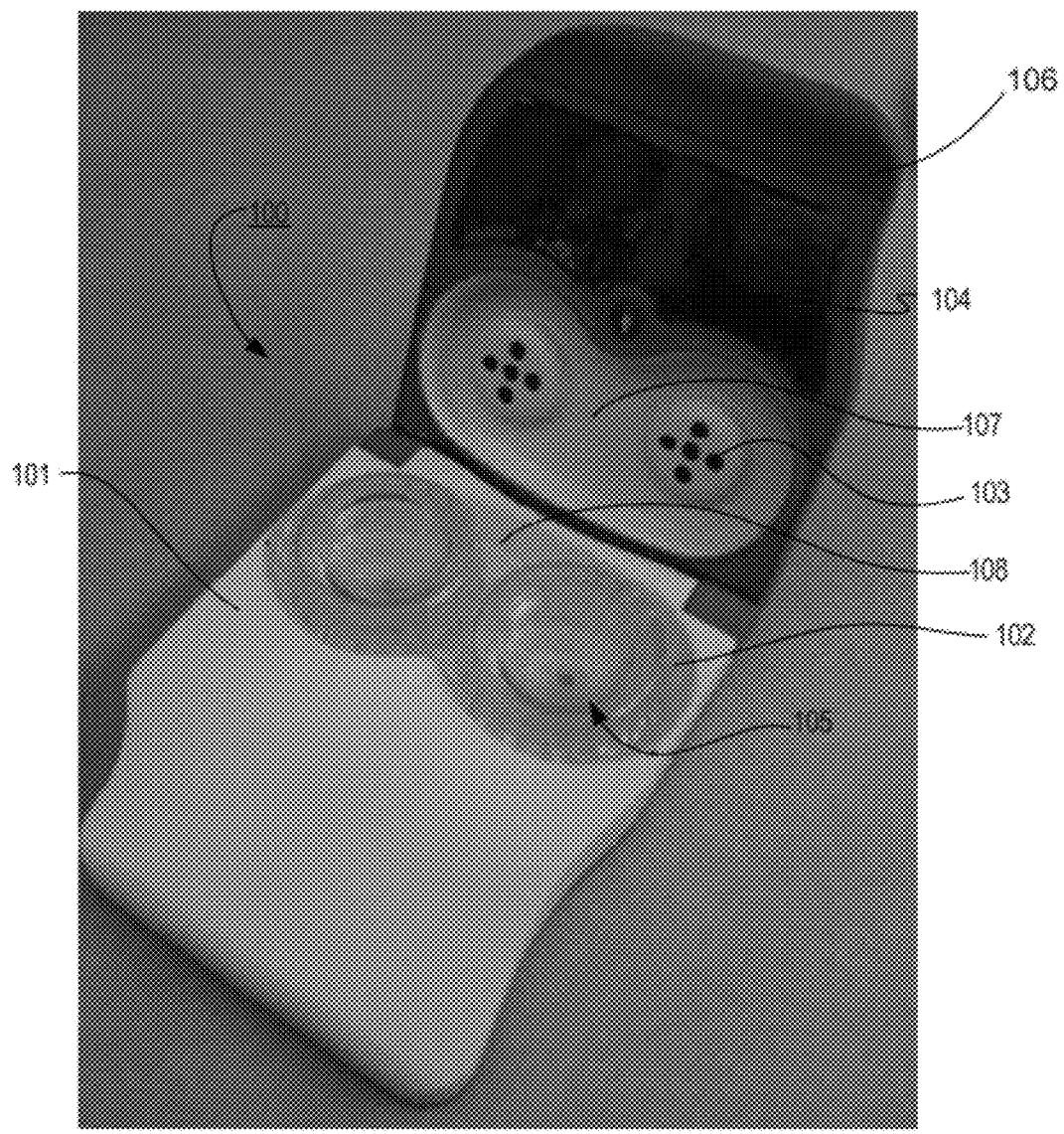
FIG. 1 illustrates an exemplary lens storage case in a base unit according to some embodiments of the present invention.

Referring now to FIG. 1, an ophthalmic lens disinfecting system 100 is illustrated including a radiation disinfecting base 101, a radiation disinfecting storage case 102 and a disinfecting radiation source 103. According to the present invention, a radiation disinfecting storage case 102 is positioned within the path of radiation from the radiation disinfecting source 103, such that one or more ophthalmic lenses stored within the radiation disinfecting storage case 102 are exposed to radiation emanating from the radiation disinfecting source 103 and life forms existing on, or in proximity to, the ophthalmic lenses are exposed to the disinfecting radiation, provided by a radiation disinfecting source, and killed, essentially disinfecting the ophthalmic lens.

As illustrated, the radiation disinfecting storage case 102 is positioned in an open state with a radiation disinfecting base 101 and a lid 106. In some preferred embodiments, the radiation disinfecting storage case 102 includes a positioning artifact 105 for aligning the disinfecting radiation source 103 with the radiation disinfecting storage case 102. As illustrated, the positioning artifact 105 includes an annular depression for receiving an annular arrangement of disinfecting radiation source 103. Positioning artifacts 105 may include almost any polygon shaped depression. Other embodiments may include one or more alignment pins. In still other embodiments, a positioning artifact 105 may include a snap, a threaded joining or other removably fixed type of joining.

In some embodiments, the positioning artifact 105 aligns the radiation disinfecting radiation source 103 in a position generally orthogonal to an apex of a contact lens stored within the radiation disinfecting storage case 102. In additional embodiments, a positioning artifact 105 aligns the radiation disinfecting radiation source 103 in a position generally orthogonal to a plane extending across a bottom perimeter of a contact lens.

In another aspect, in some embodiments, the positioning artifact may also be capable of transmitting a vibrational frequency from a radiation disinfecting base 101 to the radiation disinfecting storage case 102 and ultimately to a lens stored within the radiation disinfecting storage case 102. The vibrational frequency may be a frequency capable of causing expired life forms to be moved from within a path of radiation to an unexpired life form. Moving the expired life forms allows for more efficacious disinfecting by exposing more unexpired life forms to a direct path of radiation.

The radiation disinfecting radiation source 103 may include one or more light emitting diodes (LEDs). In some preferred embodiments, the LEDs include ultraviolet (UV) emitting LEDs. Preferred embodiments include LEDs which emit light radiation with a wavelength of between about 250 nanometers of light radiation and about 280 nanometers of light radiation, preferably, the wavelength is between 250 nanometers and 275 nanometers, and most preferably 254 nanometers.

Some embodiments include a reflective surface 107 in the lid area above the radiation disinfecting storage case 102. A reflective surface 108 may also be included in the area below the radiation disinfecting storage case 102. Reflective surfaces may include, by way of non-limiting example, Teflon® PTF-E, aluminum, magnesium oxide, zirconium oxide, and Alzak®.

Figure 2:
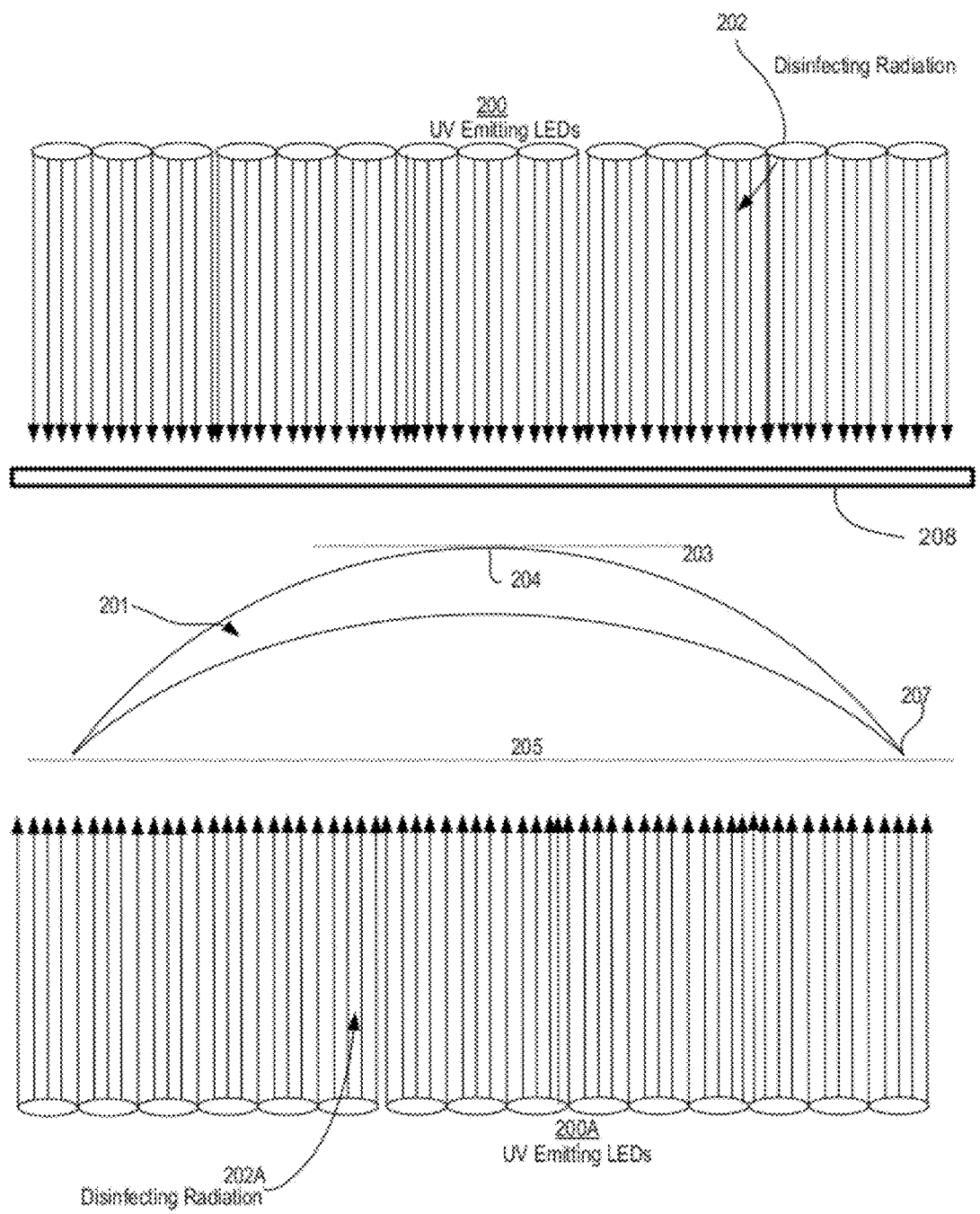
FIG. 2 illustrates some embodiments of alignment of a disinfecting radiation source with an ophthalmic lens in a lens storage case according to the present invention.

Referring now to FIG. 2, a block diagram illustrates some embodiments of alignment of a radiation disinfecting source 200, such as one or more UV LEDs radiating disinfecting radiation 202 in the UV spectrum towards a contact lens 201. In some preferred embodiments, UV LEDs will be arranged such that a radiation disinfecting storage case will align in a specific position in relation to the contact lens 201. The alignment is maintained via an alignment artifact. In some embodiments, a radiation disinfecting storage case may be aligned to direct UV radiation 202 at an angle essentially orthogonal to a plane 203 touching an apex 204 of the contact lens 201 retained in a radiation disinfecting storage case.

In other embodiments, radiation disinfecting storage case may be aligned to direct disinfecting radiation 202A from one or more UV emitting LEDs 200A at an angle essentially orthogonal to a plane 205 across a perimeter edge 207 of the contact lens 201. In other embodiments as described in FIGS.

12 and 13, radiation may be further controlled with the use of a diffusing material to ensure uniformity in things such as contrast and intensity.

In another aspect, in some embodiments, one or more optics 208 may be used to focus disinfecting radiation onto a lens stored in a disinfecting radiation storage case. An optic may be included in a base or in a part of a storage case.

Figure 3:
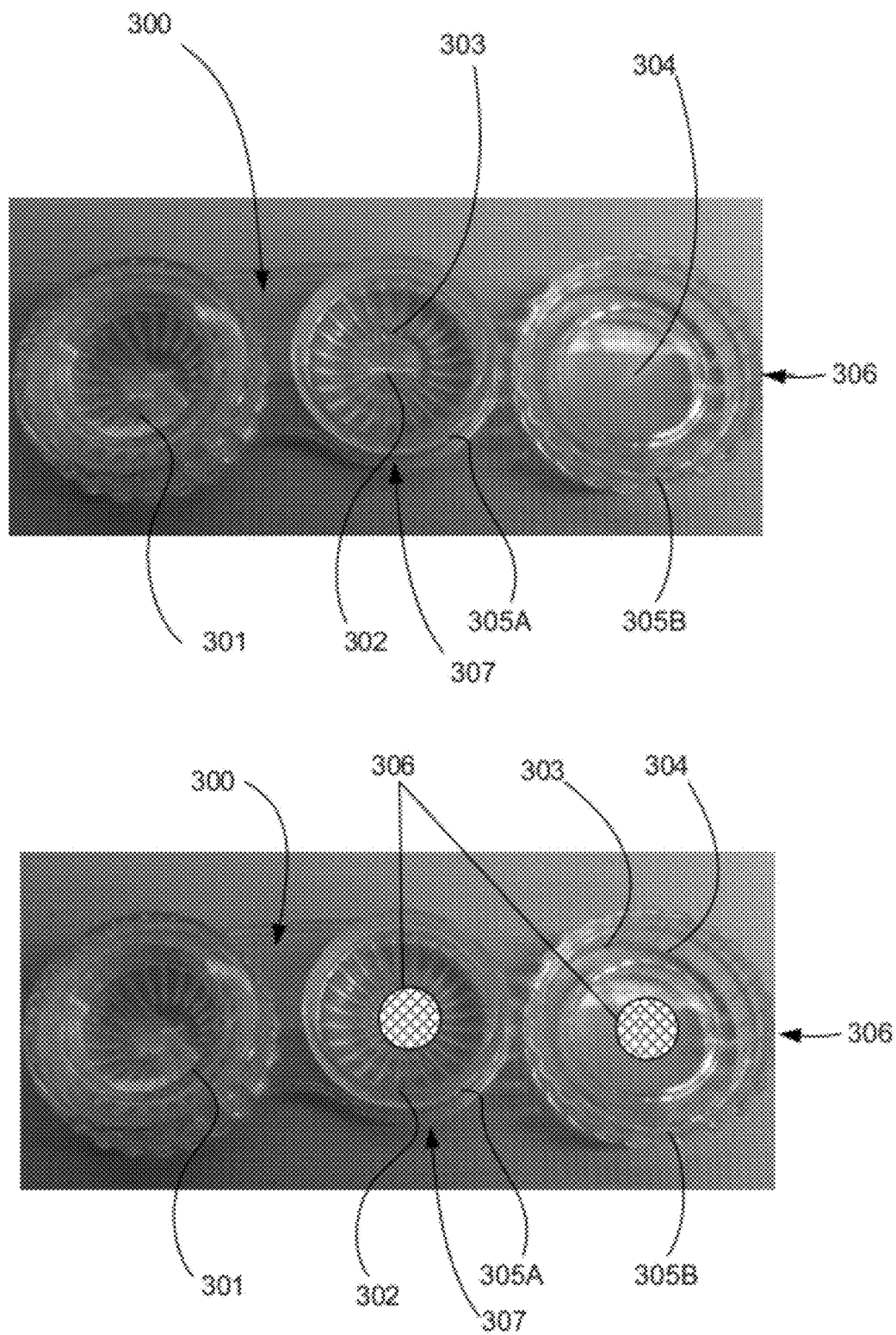
FIG. 3 illustrates a close up view of an exemplary storage case with one cap removed according to some embodiments of the present invention.

Referring now to FIG. 3, an exemplary radiation disinfecting storage case 300 is illustrated. The radiation disinfecting storage case 300 includes one or more lens storage compartments 301. A storage compartment 301 is capable of receiving and storing one or more ophthalmic lenses, such as a contact lens.

Some embodiments include one or more lens alignment mechanisms 302 for positioning an ophthalmic lens stored in a storage compartment 301 included in a radiation disinfecting storage case 300. A lens alignment mechanism 302 may include for example a pedestal with an arcuate surface generally of a similar size and shape as an inside dimension of an ophthalmic lens. A convex surface may include an arc generally equivalent to an arc of a concave surface of an ophthalmic lens to be stored within the radiation disinfecting storage case 300. Other embodiments may include a lens alignment mechanism 306 comprising a bowl generally of a similar size and shape as an outside dimension of an ophthalmic lens.

In some embodiments, positioning may align the stored lens in a direct path of disinfecting radiation. However, other embodiments may include one or reflective surfaces 306 or a radiation diffusing material. A reflective surface 306 may essentially include a mirror and be formed from a glass, a plastic, a metal or a coating that is functional to reflect disinfecting radiation in a direction desired. Generally, the direction will be towards a lens stored in a storage case 300 positioned in the base. In some embodiments, reflective surface 306 may be generally proximate to, and/or generally parallel to, a surface of a stored lens. Other embodiments may include a reflective surface 306 generally around a perimeter of a stored lens.

One or more radiation windows 303-304 are included in the storage compartments 301. The radiation windows 303-304 provide portions of the radiation disinfecting storage case that are at least partially transparent to wavelengths of disinfecting radiation. Preferably the radiation windows 303-304 will be as close to 100% transparent as possible to disinfecting radiation transmitted into the storage compartment 301. Plastics that are injection moldable may be 90% or more or even 98% or more transparent to UV radiation. Specific wavelengths may include between about 254 nanometers to 280 nanometers.

In some embodiments, a radiation window may also include an optic for directing disinfecting radiation towards areas of an ophthalmic lens stored in the stored compartment 301. In some embodiments, the whole case may be composed of a transparent material that can allow radiation to pass through and reach the lens accordingly.

Examples of materials from which the radiation windows 303-304 may be formed include, for example: cyclic olefins, TOPAS, ZEONOR® or other injection moldable plastic. Other plastics or glass may also be utilized as a material for the radiation window 303-304. The area of the radiation windows 303-304 should be sufficient to admit enough disinfecting radition into the storage compartments to kill life forms present on an ophthalmic lens stored in the storage compartment 301.

Some preferred methods of manufacture of a radiation disinfecting storage case include injection molding processes. Other methods include, for example, lathing, stereo lithography, and three dimensional printing.

In another aspect, radiation disinfecting storage case 300 may include a fastening mechanism 305A-305B for securing and removing a cap 306 from a storage compartment 307. The fastening mechanism 305A-305B may include a threaded portion, a snap, and a tapered joint of other mechanism for removably securing the cap 308 to the case at the discretion of the user. While the cap 308 is secured to the storage compartment 307, the cap seals off an ambient atmosphere from the storage compartment 307 and also contains an ophthalmic lens and, in some embodiments, a solution, such as, for example a saline solution, within the compartment 307.

Figure 4:
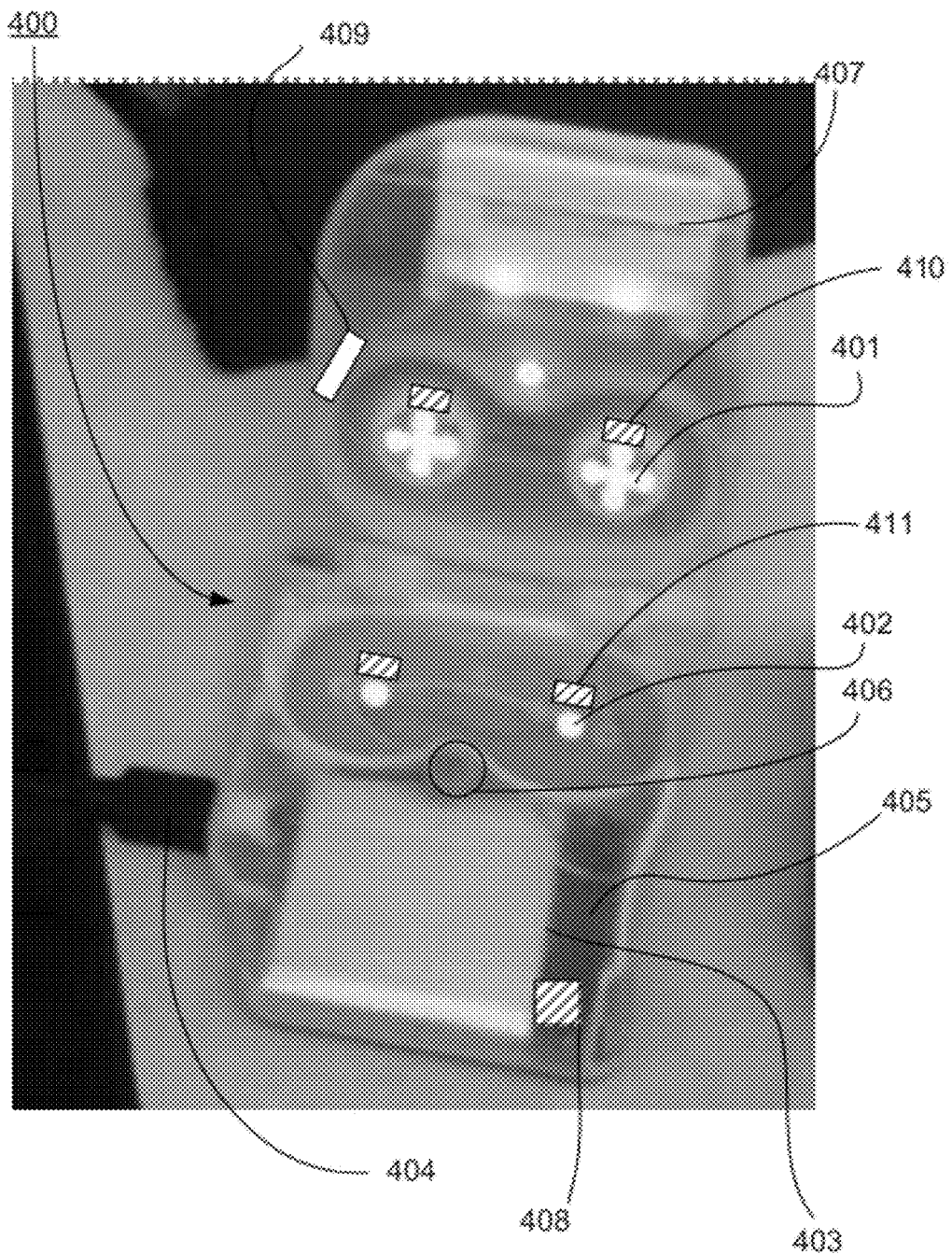
FIG. 4 illustrates aspects of a base unit according to some embodiments of the present invention.

Referring now to FIG. 4, a radiation disinfecting base unit 400 is illustrated with multiple disinfecting radiation source LEDs 401-402. As illustrated, the disinfecting radiation source LEDs 401-402 may include one or both of overhead disinfecting radiation source LEDs 401 and lower disinfecting radiation source LEDs 402. In addition to the overhead disinfecting radiation source LEDs 401 and lower disinfecting radiation source LEDs 402, the base unit may include a processor board 403 with control electronics for controlling various aspects associated with the radiation disinfecting base 400.

The processor board 403 may be coupled to a digital storage 408. The digital storage may include executable software that is executable upon command or automatically upon operation of the radiation disinfecting base unit 400. The digital storage 408 may also store data related to operation of the radiation disinfecting case 400. Operational data may include for example, time periods during which a radiation disinfecting base unit 400 is operated; serial numbers of lenses being disinfected; a period of time that a lens has been placed in use, or other information. In some embodiments, a radiation disinfecting base unit 400 may include a scanner 409 or other input means to input an identification number associated with a lens stored in a radiation disinfecting base unit 400. For example, the scanner 409 may scan a bar code or other symbol on a lens package and log disinfecting information associated with the bar code number or symbol. Information that may be logged may include for example, a number of hours that a lens has been exposed to disinfecting radiation and a number of days that a lens has been placed into use.

In some embodiments, one or more of the disinfecting radiation source LEDs 401-402 may include integrated LED sensors. Other embodiments may include one or both of overhead LED sensors and lower LED sensors that are discrete from disinfecting radiation source LEDs 401-402. LED sensors may be in logical communication with a processor board 403 which may store data in digital storage 408.

In another aspect, in some embodiments, one or more of overhead CCD image sensors 410 or lower CCD image sensors 411 may be included in a radiation disinfecting base unit 400. CCD image sensors 410-411 may be in logical communication with a processor board 403 which may store data in digital storage 408.

The processor board 403 may analyze one or both of LED sensor data and CCD image sensor data for purposes including, but not limited to, detecting if disinfecting radiation source LEDs 401-402 are functional, detecting if disinfecting radiation source LEDs 401-402 are operating at acceptable levels, detecting if a radiation disinfecting storage case is present in a radiation disinfecting base unit 400, detecting if a contact lens or contact lenses are present within a radiation disinfecting storage case, detecting contact lens cleanliness, determining if new contact lenses have been inserted in a radiation disinfecting storage case based on a comparison of previous lens cleanliness data and current lens cleanliness data, detecting correct placement of right and left contact lenses within a radiation disinfecting storage case when the user wears two different lens powers, and detecting lens brand based on comparison of two UV readings against profile signatures for different lens brands.

An electrical communication connector 404 may also be included in the radiation disinfecting base unit 400. The electrical communication connector 404 may include a universal serial bus (USB) connector or other type of connector. The connector may include a terminal for transferring one or both of data and electrical power. In some embodiments, the electrical communication connector 404 provides power to operate the radiation disinfecting base unit 400. Some embodiments may also include one or more batteries 405 or other power storage device. In some preferred embodiments, the batteries 405 include one or more lithium ion batteries or other rechargeable device. The power storage devices may receive a charging electrical current via the electrical communication connector 404. Preferably, the radiation disinfecting base unit 400 is operational via stored power in the batteries 405.

In some embodiments, the electrical communication connector 404 may include a simple source of AC or DC current.

In another aspect, the present invention may include a source of mechanical movement, such as a vibration generation device 406. The vibration generation device 406 may include, for example, a piezoelectric transducer. A piezoelectric transducer offers a low power reliable device to provide mechanical or vibrational movement.

In some embodiments, the vibrational movement will be adjusted to a frequency that effectively moves dead organisms stored within a storage case in the radiation disinfecting base unit 400. Movement of the dead organisms exposes live organisms that may have otherwise been sheltered from disinfecting radiation. In another aspect, the vibrational movement will be adjusted to a frequency that effectively removes protein from contact lenses stored within a radiation disinfecting case. Protein removal may occur at the same vibrational frequency as organism removal, or at a different frequency.

In still another aspect, in some embodiments, the processor board 403 or other electronic circuitry may control a pattern of light or radiation emitted by the disinfecting radiation source LEDs 401-402. The light pattern may include, for example, pulsed UV or other form of strobed radiation of one or both of a set frequency or variable frequencies, wherein at least some of the frequencies are suitable for disinfecting microbes. Various embodiments may include one or more of: continuous wave cycles; continuous square wave cycles; variable wave cycles; and variable square wave cycles.

In some preferred embodiments, disinfecting radiation source LEDs 401-402 provide power in the range of 50 microwatts to 5 watts. Equivalent doses of disinfecting radiation may be applied using continuous low power over an extended period of time, or using pulsed UV in which short bursts of high power are spread over time, most preferably a shorter period of time than used in continuous UV. Pulsed UV may be used to achieve more effective microbial extermination than continuous UV with an equivalent or smaller UV dose.

The processor board 403 or other electronic circuitry may additionally adjust light patterns, disinfecting cycle time, and disinfecting intensity based on factors including but not limited to a number of times a lens has been disinfected, an amount of time since a lens was first disinfected, sensed lens cleanliness, and current bulb performance.

Some embodiments may also include a display 407. The display 407 will be in logical communication with the processor board 403 and be used to communicate, in human readable form, data relating to the operation of the radiation disinfecting base unit 400.

Figure 5:
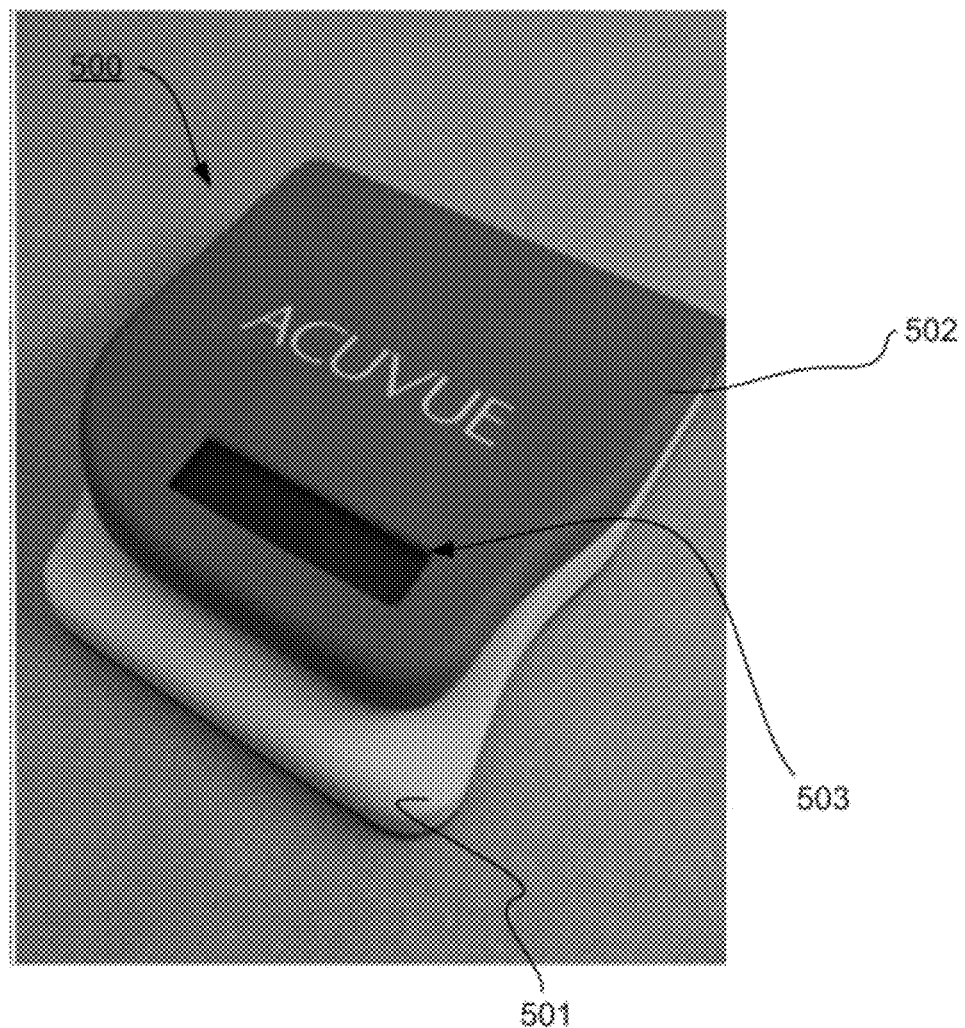
FIG. 5 illustrates a base unit in a closed state with a display.

Referring now to FIG. 5, a radiation disinfecting base unit 500 is illustrated in a closed position. A radiation disinfecting base 501 is covered by a lid 502, in the illustrated embodiments; the lid 502 is hinged to the radiation disinfecting base 501 and folds over on top of the radiation disinfecting base 501. Other embodiments are also within the scope of the invention. As illustrated, a display 503 can be located in the lid 502 and may provide an indication of a disinfecting cycle or procedure being executed by the radiation disinfecting base unit 500.

Figure 6A:
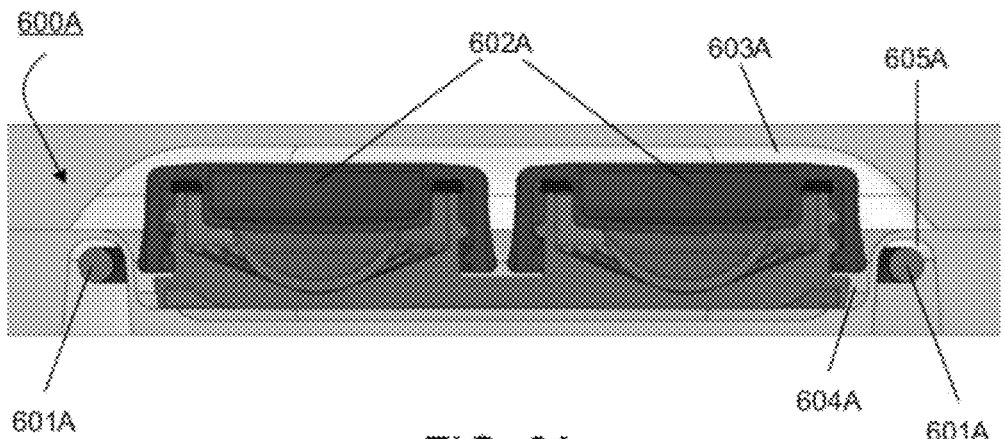
FIG. 6A illustrates a cut-away view of a portion of a base unit with a germicidal bulb surrounding a lens storage case compartment according to some embodiments of the present invention.

Referring now to FIG. 6A, a cut-away view of a portion of a radiation disinfecting base unit 600A is illustrated with a disinfecting radiation source germicidal bulb 601A. As illustrated, a germicidal bulb 601A may be contained within the radiation disinfecting base unit 600A generally encircling the compartment containing the radiation disinfecting storage case 602A. Some embodiments include a reflective surface 603A in the lid area above the radiation disinfecting storage case 602A. A reflective surface 604A may also be included in the area below the radiation disinfecting storage case 602A. Additionally, the germicidal bulb cavity 605A may incorporate a reflective surface. Reflective surfaces may include, by way of non-limiting example, Teflon® PTF-E, aluminum, magnesium oxide, zirconium oxide, and Alzak®

Figure 6B:
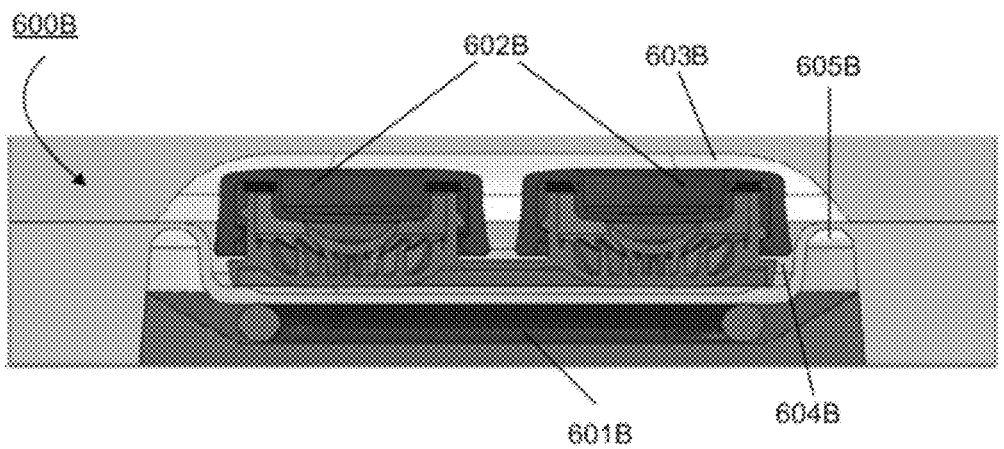
FIG. 6B illustrates a cut-away view of a portion of a base unit with a germicidal bulb beneath a lens storage case compartment according to some embodiments of the present invention.

In another exemplary embodiment, FIG. 6B depicts a cut-away view of a portion of a radiation disinfecting base unit 600B with a disinfecting radiation source germicidal bulb 601B positioned below the compartment containing the radiation disinfecting storage case 602A. Reflective surfaces 603B and 604B may be present above and below the radiation disinfecting storage case 602B respectively, as well as in the germicidal bulb cavity 605B.

In still other embodiments, a germicidal bulb may be contained within the lid of a radiation disinfecting base unit. Further embodiments may include multiple germicidal bulbs in a radiation disinfecting base unit, including in a lower portion of the base unit, a lid portion, or both. Germicidal bulbs may be present in a radiation disinfecting base unit in place of or in addition to UV LED bulbs that have been described in prior figures.

A germicidal bulb may include, by way of non-limiting example, a low pressure mercury vapor bulb or a medium pressure mercury vapor bulb. In some preferred embodiments, the germicidal bulb emits ultraviolet light radiation. Preferred embodiments of the germicidal bulb emit ultraviolet (UV) light radiation with a wavelength of between about 250 nanometers of light radiation and about 280 nanometers of light radiation, preferably, the wavelength is between about 250 nanometers and 275 nanometers, and most preferably about 260 nanometers.

Non-LED components described in earlier figures, including but not limited to positioning artifacts, reflective surfaces, vibration generation device, optics to focus radiation, processor board, digital storage, scanner, electrical connector, batteries, and display, may be included in a disinfecting base unit with germicidal bulb.

Although the pulsed UV method may not be preferred with a germicidal bulb, a processor board or other electronic circuitry included in a radiation disinfecting base unit 600A or 600B may adjust light patterns, disinfecting cycle time, and disinfecting intensity based on factors including but not limited to a number of times a lens has been disinfected, an amount of time since a lens was first disinfected, and sensed lens cleanliness.

Figure 7:
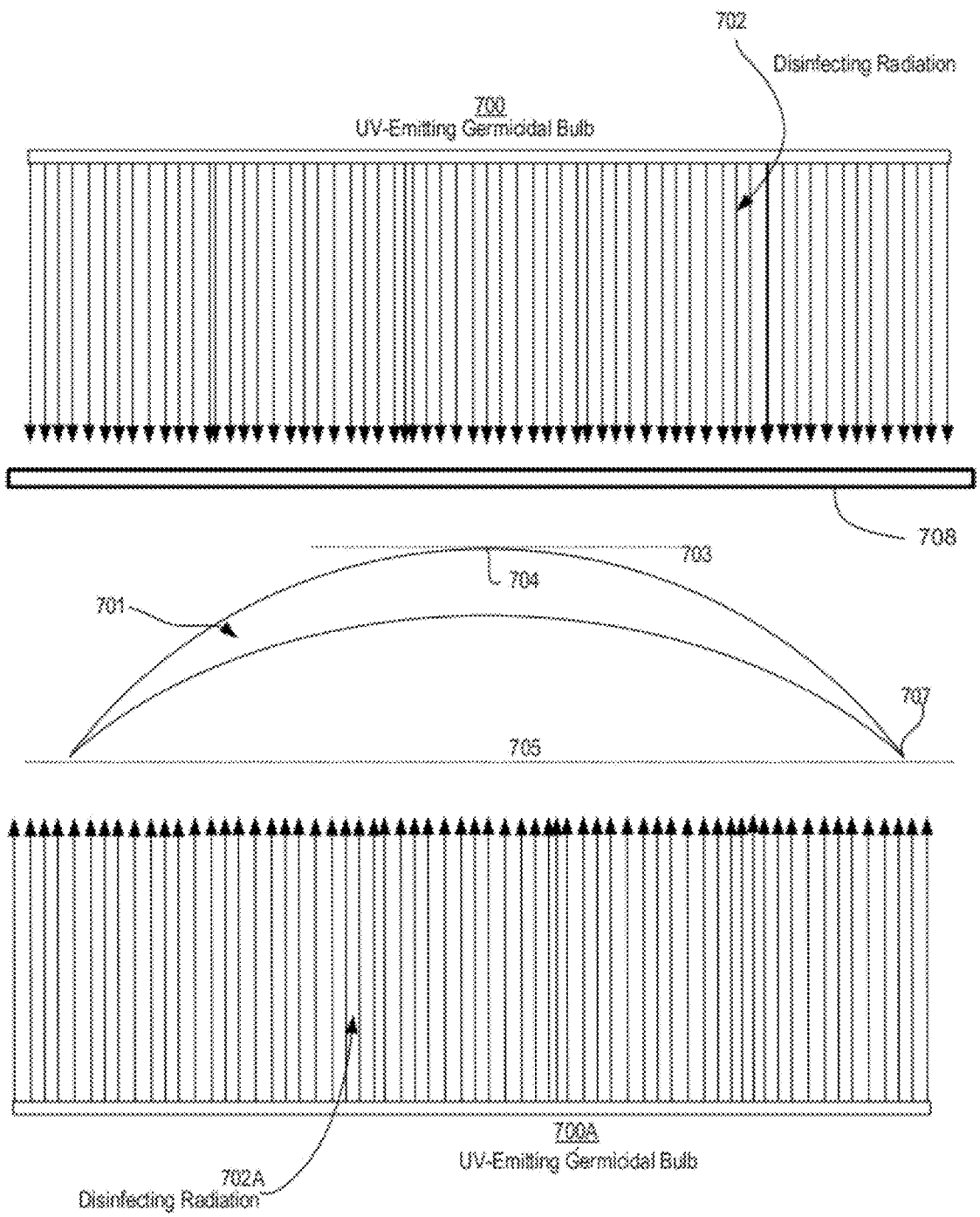
FIG. 7 illustrates some embodiments of alignment of a disinfecting radiation source germicidal bulb with an ophthalmic lens in a lens storage case according to the present invention.

Referring now to FIG. 7, a block diagram illustrates some embodiments of alignment of a radiation disinfecting source 700, such as one or more germicidal bulbs radiating disinfecting radiation 702 in the UV spectrum towards a contact lens 701. In some preferred embodiments, germicidal bulbs will be arranged such that a radiation disinfecting storage case will align in a specific position in relation to the contact lens 701. The alignment is maintained via an alignment artifact. In some embodiments, a radiation disinfecting storage case is aligned to direct UV radiation 702 at an angle essentially orthogonal to a plane 703 touching an apex 704 of the contact lens 701 retained in a radiation disinfecting storage case.

In other embodiments, radiation disinfecting storage case may be aligned to direct disinfecting radiation 702A from one or more UV emitting germicidal bulbs 700A at an angle essentially orthogonal to a plane 705 across a perimeter edge 707 of the contact lens 701.

In another aspect, in some embodiments, one or more optics 708 may be used to focus disinfecting radiation onto a lens stored in a disinfecting radiation storage case. An optic may be included at a variety of positions within the path of radiation, some exemplary locations may include: in a base; in a part of a storage case; and as part of a radiation source, such as an LED or bulb.

Figure 8:
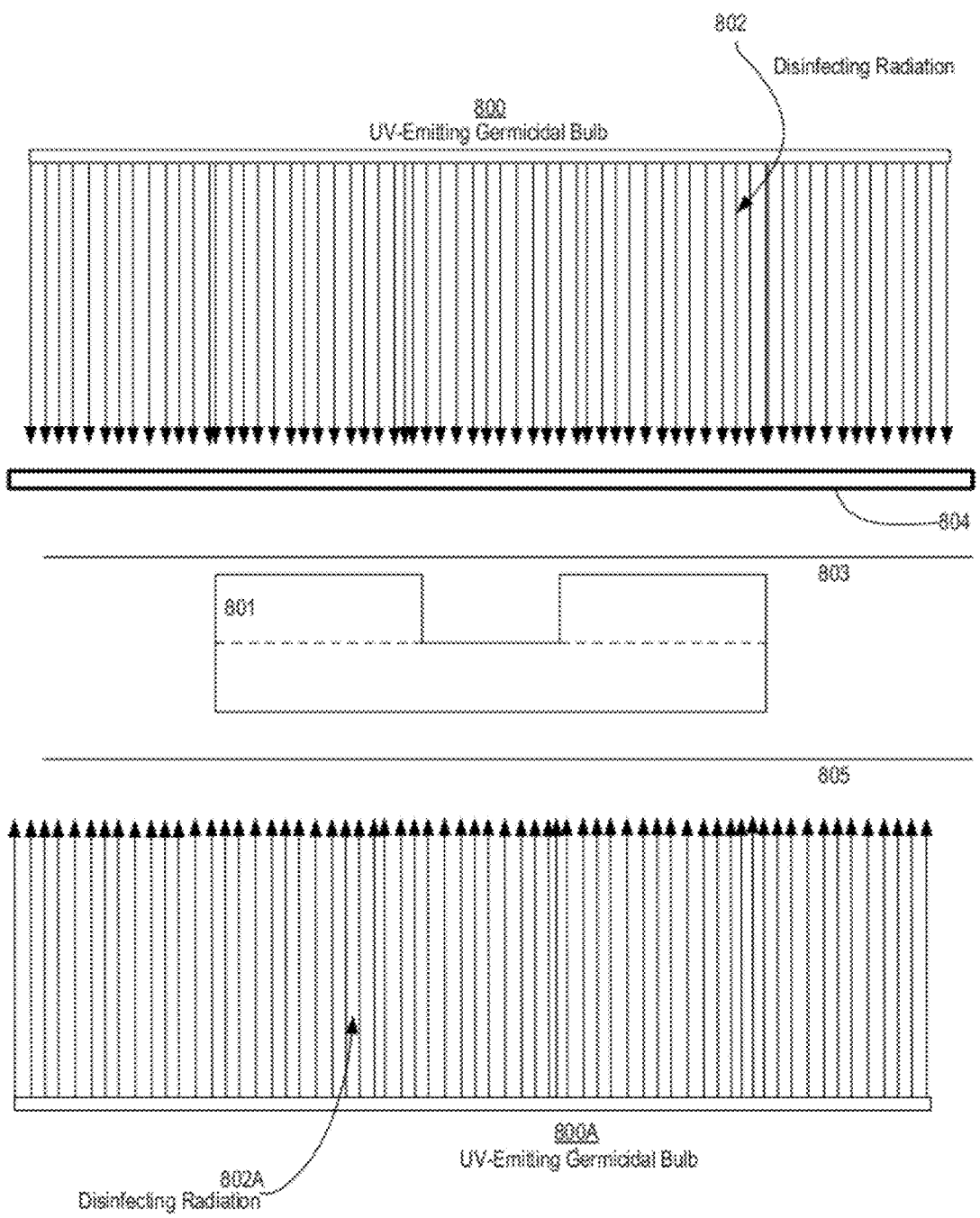
FIG. 8 illustrates some embodiments of alignment of a disinfecting radiation source germicidal bulb with a lens storage case according to the present invention.

Referring now to FIG. 8, a block diagram illustrates some embodiments of alignment of a radiation disinfecting source 800, such as one or more germicidal bulbs radiating disinfecting radiation 802 in the UV spectrum towards a contact lens storage case 801. In some preferred embodiments, germicidal bulbs will be arranged such that a radiation disinfecting storage case will align in a specific position in relation to the contact lens storage case 801. The alignment is maintained via an alignment artifact.

In some embodiments, a radiation disinfecting storage case is aligned to direct UV radiation 802 at an angle essentially orthogonal to a plane 803 plane across a top portion of the contact lens storage case 801.

In other embodiments, radiation disinfecting storage case may be aligned to direct disinfecting radiation 802A from one or more UV emitting germicidal bulbs 800A at an angle essentially orthogonal to a plane 805 across one or both of a bottom and a top of the contact lens storage case 801.

In another aspect, in some embodiments, one or more optics 804 may be used to focus disinfecting radiation onto a disinfecting radiation storage case 801. An optic may be included in a base or in a part of a storage case.

Figure 9:
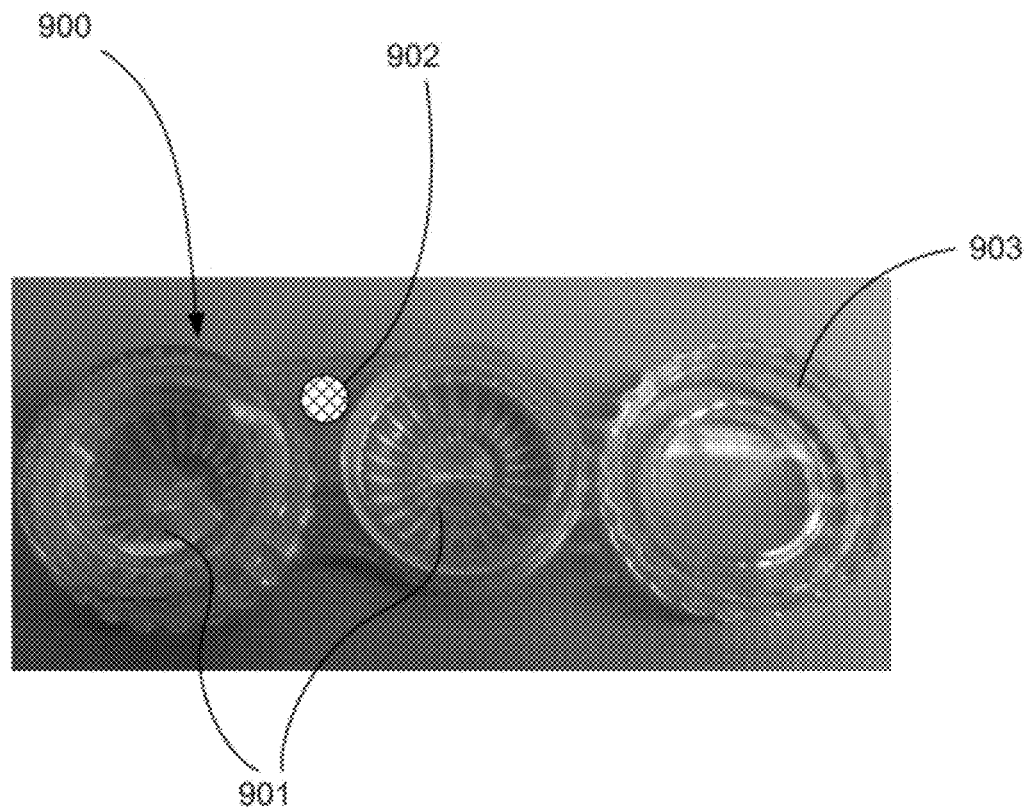
FIG. 9 illustrates a close up view of a storage case with a change indicator according to some embodiments of the present invention.

Referring now to FIG. 9, an exemplary radiation disinfecting storage case with change indicator 900 is illustrated. The radiation disinfecting storage case with change indicator 900 includes one or more lens storage compartments 901. A storage compartment 901 is capable of receiving and storing one or more ophthalmic lenses, such as a contact lens. As illustrated, a change indicator 902 may be included on a ledge of the radiation disinfecting storage case with change indicator 900, generally between the two lens storage compartments 901. In other embodiments, a change indicator 902 may include a ring encircling one or both lens storage compartments 901, an area on a lens storage compartment cap 903, an area on or completely encircling the radiation disinfecting storage case with change indicator 900, or other location within the radiation disinfecting storage case with change indicator 900 or lens storage compartment cap 903.

In some embodiments, a change indicator 902 may be comprised of dye within or on the plastic or other material from which the radiation disinfecting storage case with change indicator 900 or lens storage compartment cap 903 is made. In other embodiments, a change indicator 902 may be a material embedded in or adhered to the radiation disinfecting storage case with change indicator 900 or lens storage compartment cap 903.

A change indicator 902 dye or material will change color or texture or both color and texture to indicate that the user should discard the current radiation disinfecting storage case with change indicator 900 and begin using a new one. The change indicator 902 color or texture may transform gradually over a period of time until it reaches a state generally recognized by the user as evidence that the radiation disinfecting storage case with change indicator 900 should be discarded.

Figure 10:
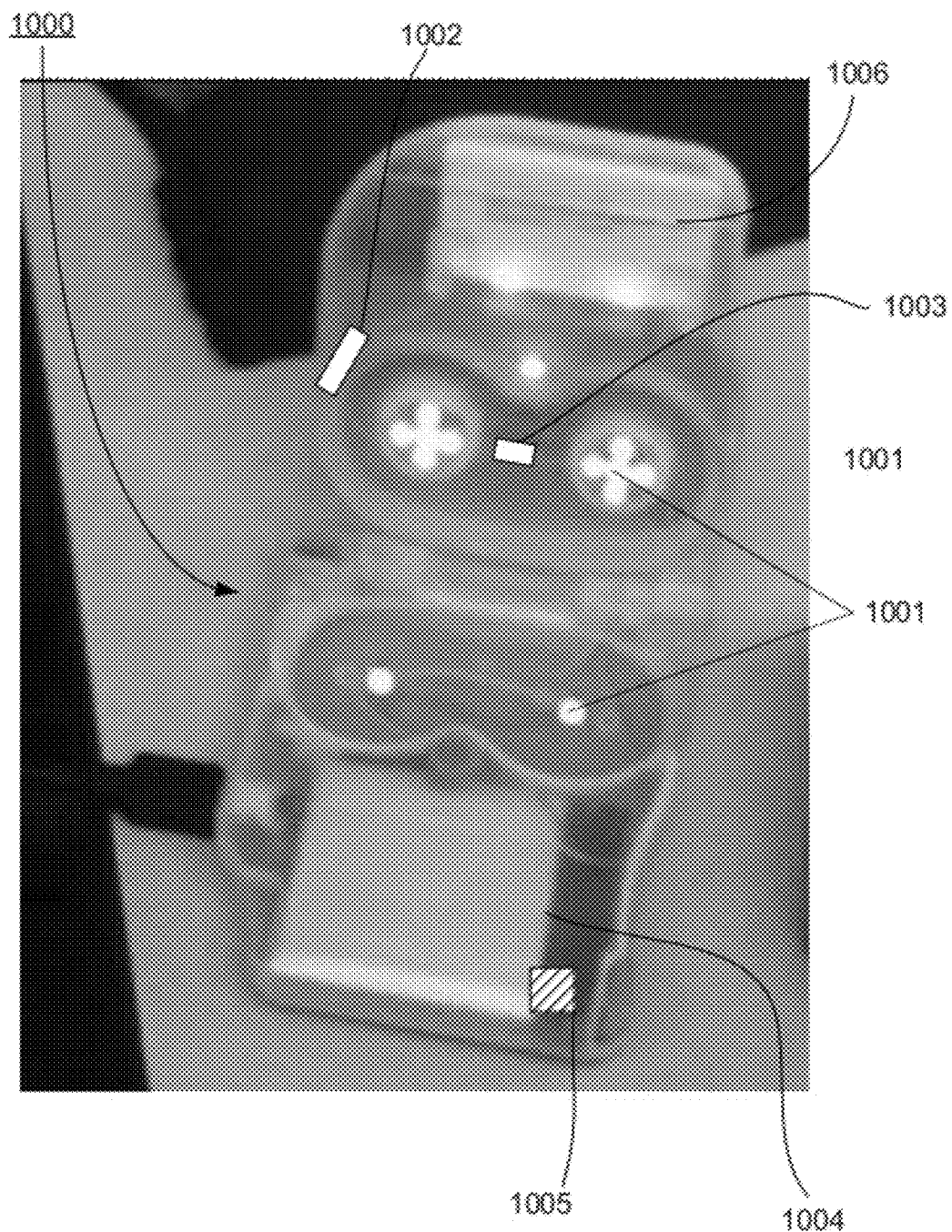
FIG. 10 illustrates aspects of a base unit with sensors to capture information about the state of a storage case change indicator according to some embodiments of the present invention.

Referring now to FIG. 10, a radiation disinfecting base unit 1000 is illustrated with one or more of an LED sensor 1001, a scanner 1002, and a camera 1003. An LED sensor 1001, scanner 1002, or camera 1003 captures information about the state of a change indicator on a radiation disinfecting storage case, as described in FIG. 9.

A digital storage 1005, which may be attached to, or otherwise in logical communication with the processor board 1004, may store change indicator data. In some embodiments, the processor board 1004 compares the change indicator data to previously stored change indicator data to identify a magnitude of change in the data. A specified magnitude of change determines when it is time to change a radiation disinfecting storage case. In other embodiments, the processor board 1004 compares current change indicator data to stored target data to determine when a radiation disinfecting storage case should be changed. When the processor board 1004 logic determines that a radiation disinfecting storage case should be changed, the processor board 1004 causes a message to be displayed to the user on a display 1006.

In some embodiments, a radiation disinfecting base unit 1000 with processor board 1004 and digital storage 1005 are used to track the age, usage, or other criteria relevant to a radiation disinfecting storage case. For example, age may be tracked based on the date a new radiation disinfecting storage case was inserted into the radiation disinfecting base unit 1000. Usage may be determined based on a number of disinfecting cycles that have occurred since a new radiation disinfecting storage case was inserted. When process board 1004 logic determines, based on age, usage, or other criteria, that a radiation disinfecting storage case should be changed, an appropriate user message is included on the display 1006.

In still other embodiments, processor board 1004 logic will analyze multiple variables related to a radiation disinfecting storage case, including by way of non-limiting example change indicator data, age records, usage figures, or other relevant information. The processor board 1004 logic will include algorithms to identify a combination of variables indicating a radiation disinfecting storage case should be changed. The processor board 1004 will then cause a message to be presented on the display 1006 informing the user it is time to change the radiation disinfecting storage case.

Figure 11A:
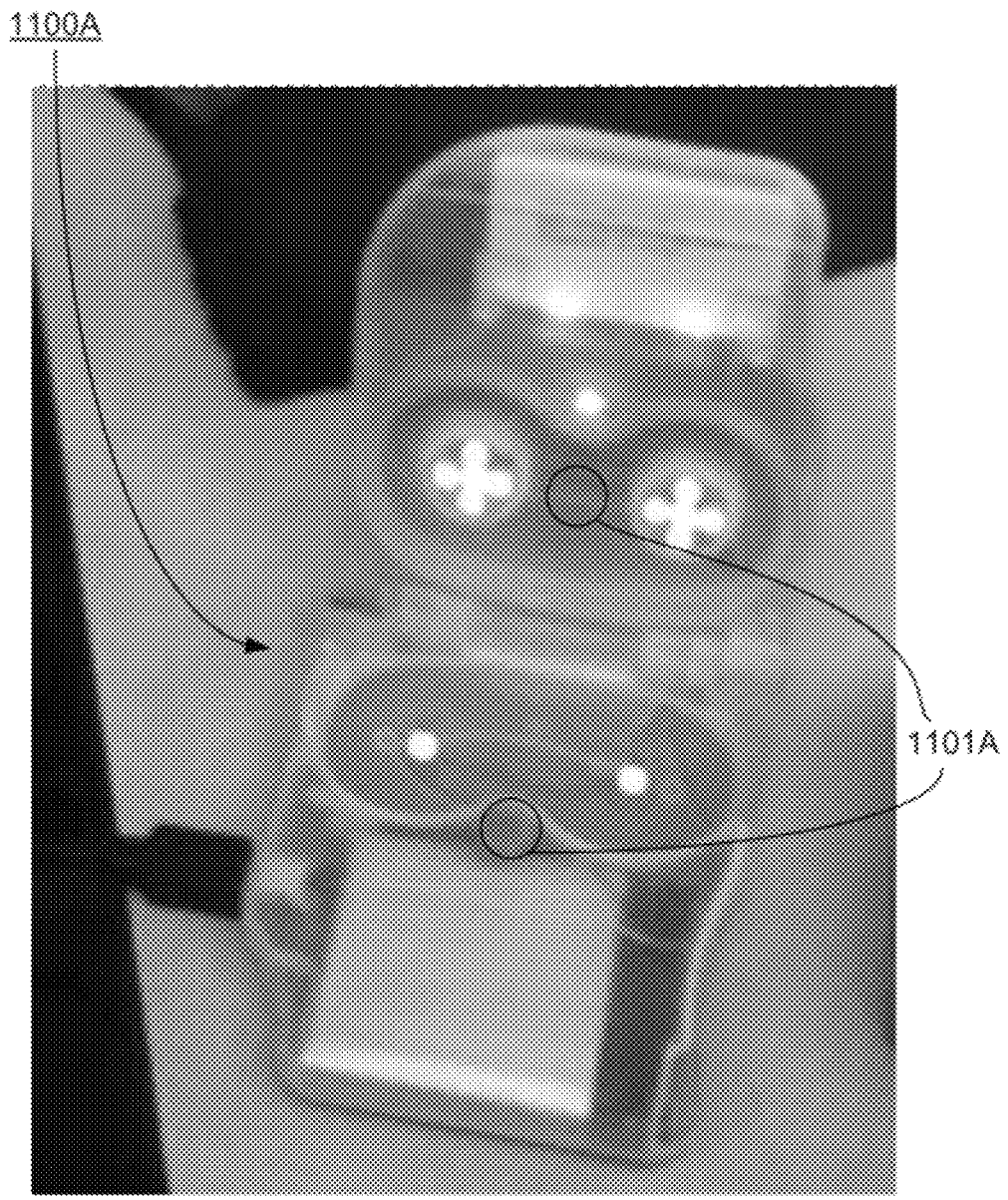
FIG. 11A illustrates aspects of a base unit with an electromagnet to impart vibrational movement according to some embodiments of the present invention.

Referring now to FIG. 11A, a radiation disinfecting base unit 1100A is depicted with an electromagnet 1101A in the lower portion of the base unit. In other embodiments, an electromagnet 1101A may be placed in a lid of a radiation disinfecting base unit 1100A.

Figure 11B:
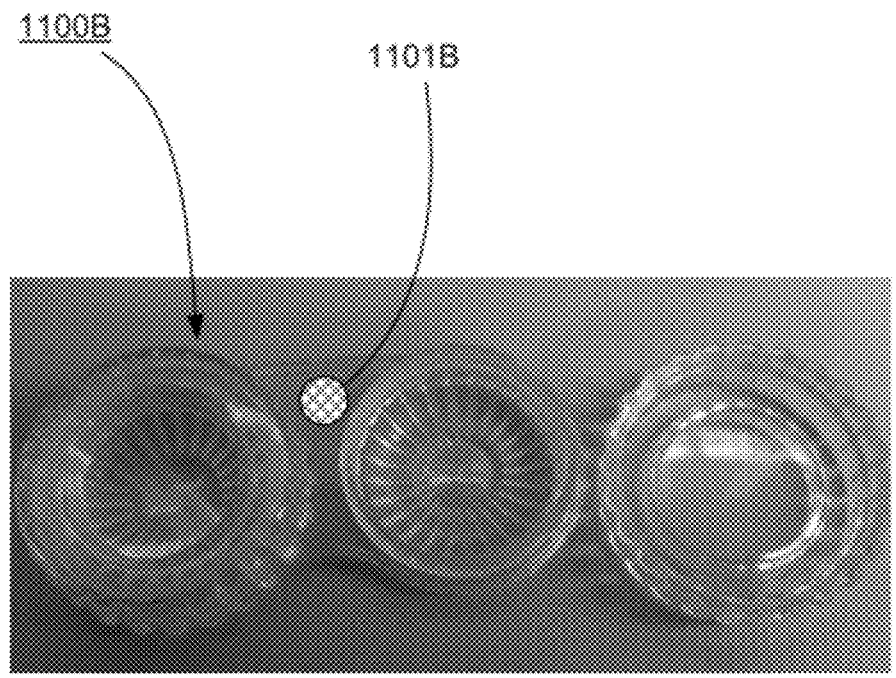
FIG. 11B illustrates a close up view of a storage case with a magnet or metallic area to effect vibrational movement according to some embodiments of the present invention.

Referring now to FIG. 11B, a radiation disinfecting storage case 1100B includes a permanent magnet 1101B. When a radiation disinfecting storage case 1100B with permanent magnet 1101B is present in a radiation disinfecting base unit 1100A, electrical current may be applied and removed from an electromagnet 1101A, causing attraction and repulsion of a permanent magnet 1101B and resulting in vibration of the radiation disinfecting storage case 1100B. Adjustment of an electrical current applied to an electromagnet 1101A allows control of one or more of frequency and amplitude of vibration. In some embodiments, a non-magnetic metallic area is implemented in place of a permanent magnet 1101B, where the non-magnetic metallic area may be attracted by an electromagnet 1101A resulting in vibration of a radiation disinfecting storage case 1100B.

In some embodiments, the vibrational movement will be adjusted to a frequency that effectively moves dead organisms stored within a radiation disinfecting storage case 1100B, and from contact lenses contained therein. Movement of the dead organisms exposes live organisms that may have otherwise been sheltered from disinfecting radiation. In another aspect, the vibrational movement will be adjusted to a frequency that effectively removes protein from contact lenses stored within a radiation disinfecting case. Protein removal may occur at the same vibrational frequency as organism removal, or at a different frequency.

In some embodiments with the use of one or more, or a combination of, disinfecting radiation sources, such as disinfecting LEDs or germicidal bulbs, a Diffusing Material may be used. The Diffusing Material can help ensure that an even distribution of radiation is received by the lens being disinfected, as it may be important to ensure proper disinfection results. Diffusing materials, such as for example, a fluoropolymer can be capable of diffusing radiation while not significantly degrading and can be at least partially transmissive to disinfecting radiation so that disinfecting radiation can reach all parts of the lens accordingly. In one aspect, a fluoropolymer can minimize contrast issues that would prevent even disinfection. In another aspect, a fluoropolymer such as FEP for example, may be injection molded into geometries capable of enclosing the case. This can allow for easy incorporation of said diffusing material in the base.

Figure 12:
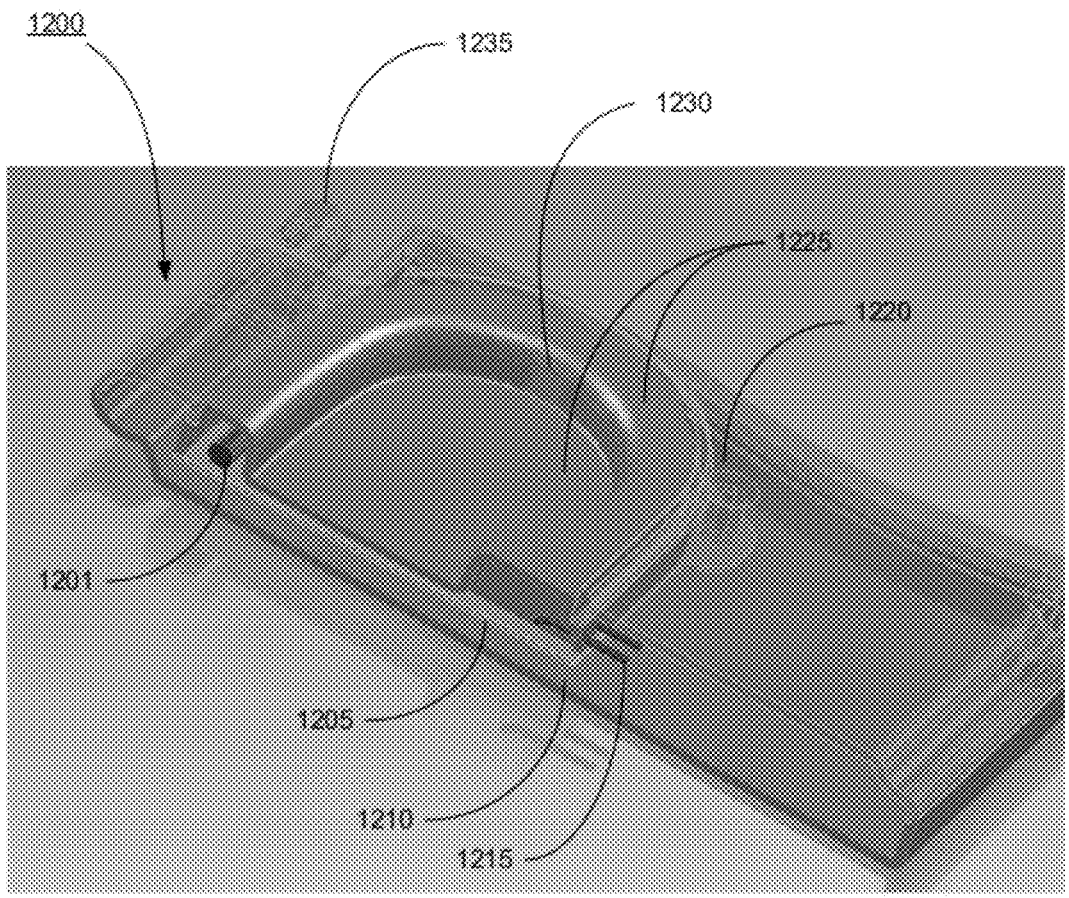
FIG. 12 illustrates a cross section of an exemplary geometry and configuration for a radiation diffusing material in the disinfection base.

Referring now to FIG. 12, a cross section of an exemplary geometry and configuration for a radiation diffusing material in the disinfection base 1200 is illustrated. At 1201, a circulating germicidal bulb is depicted. Around the germicidal bulb 1201, diffusing material 1225 may be used. At 1215, the lead for the bulb is depicted.

Additionally in some embodiments, a reflective surface 1205 may also be used to aid in the distribution of radiation along with the diffusing material and increase efficiency of the device. At 1230, one or more sensor may be placed in the diffusing material to help measure the radiation being delivered to the lens at specific regions. This may be achieved with the use of the processor and a feedback loop system as known in the art. In some embodiments, measuring the diffused radiation may allow a processor to increase or decrease the intensity or time of the disinfecting radiation.

In some embodiments, a circuit board 1210 for the processor may be placed below the reflective material 1205. Other components may be included such as a camera, focusing optical lenses, alignment artifacts, and vibration components as previously discussed to ensure improved disinfection. Additionally in preferred embodiments, the geometry of the base may be so that the diffusing material can envelop the disinfecting case, thereby providing more uniform disinfecting radiation throughout all areas of the lens. Moreover, in some embodiments, the diffusing material may be contained in at least portions the case as it may be desired.

Figure 13:
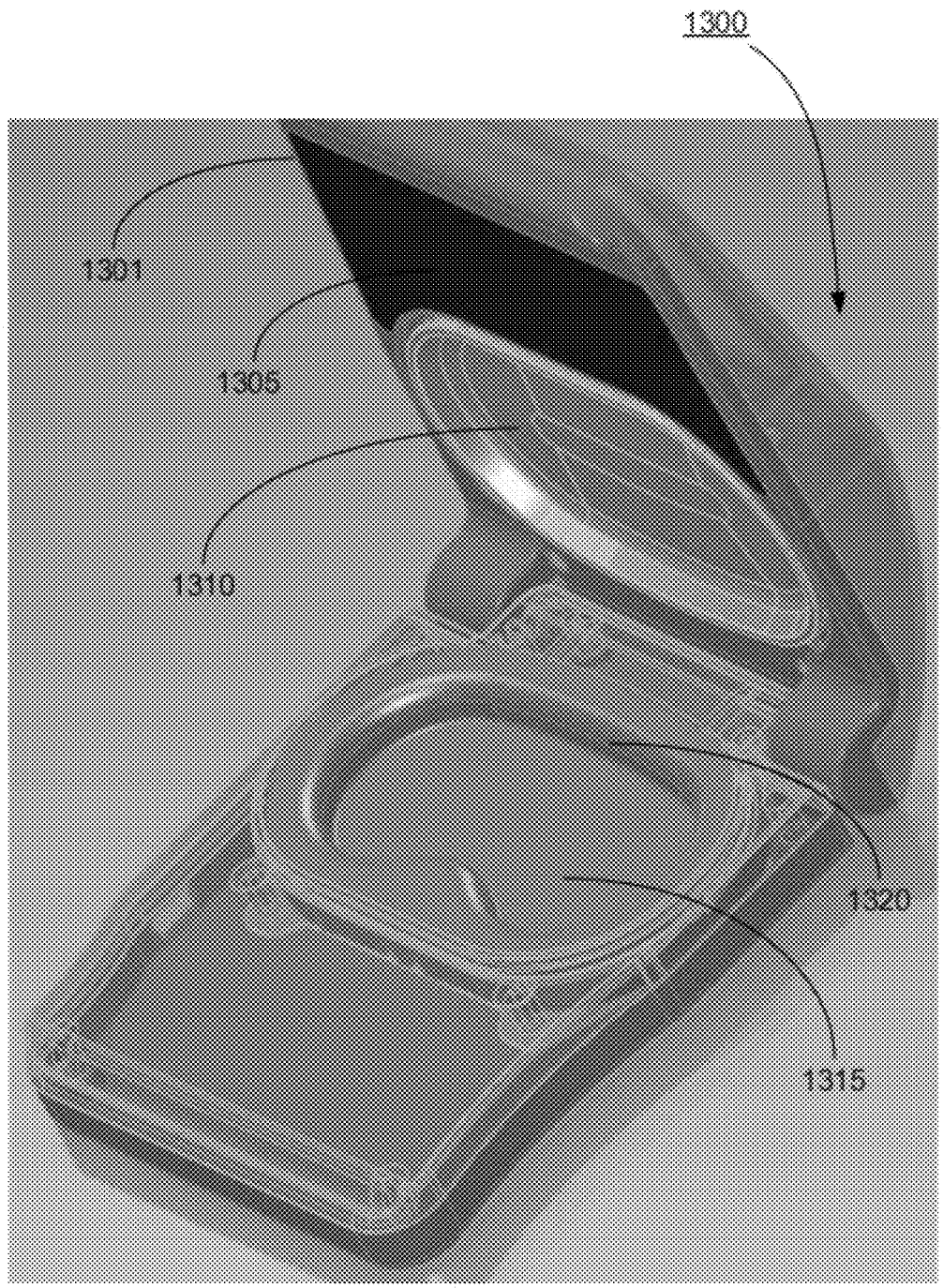
FIG. 13 illustrates an exemplary embodiment that illustrates a disinfection base with a lid comprising UV diffusing material and reflective surfaces.

FIG. 13 illustrates an exemplary embodiment 1300 that illustrates a disinfection base with a lid comprising UV diffusing material and reflective surfaces. At 1310, 1315, and 1320 diffusing material is depicted. Specifically 1320 depicts a geometry that may be used to envelop the case and align the case when placed inside the base. At 1305, a magnet or some soft pad material may be placed in the lid 1301 to avoid unwanted noise from the friction caused by any vibration in the device. The padding material may additionally help contain the radiation thereby preventing visibility through the groove formed between the base and the base lid as it may be desired. Also in some embodiments where a touch screen display is used as an interphase, the padding material 1305 may be capable of reflecting or containing the radiation to protect the display from degrading from the radiation.

CONCLUSION

The present invention, as described above and as further defined by the claims below, provides apparatus for disinfecting an ophthalmic lens.

The invention claimed is:

1. In combination:
an ophthalmic lens storage case containing at least one ophthalmic corrective lens for use in or on the eye; and
a base for receiving said ophthalmic lens storage case, the base comprising:
a receptacle for receiving said ophthalmic lens storage case;
a source of disinfecting radiation proximate to the storage case; and
a diffusing material between the disinfecting radiation source and said at least one ophthalmic corrective lens in the ophthalmic lens storage case; and
additionally comprising a vibration generation device for providing mechanical movement to a storage case placed in the storage base.

2. The combination of claim 1 wherein the diffusing material comprises a fluoropolymer.

3. The combination of claim 1 wherein the diffusing material is shaped to envelop the shape of the case.

4. The combination of claim 1 additionally comprising a reflective surface for reflecting disinfecting radiation towards ophthalmic lens storage compartment, wherein the reflective surface comprises one or more of: Teflon®, aluminum, magnesium oxide and zirconium oxide.

5. The combination of claim 1 additionally comprising an optical quality material capable of focusing the radiation to at least a portion of the diffusing material.

6. The combination of claim 1 wherein the disinfecting radiation source comprises one or more light emitting diodes emitting ultraviolet radiation.

7. The combination of claim 1 wherein the disinfecting radiation source comprises one or more germicidal bulbs.

8. The combination of claim 7 wherein the germicidal bulb(s) has a shape circulating one or more storage compartment(s) of the lens storage case.

9. The combination of claim 1 additionally comprising a mechanism for causing the one or more of the disinfecting sources to pulse ultraviolet radiation, wherein the pulsing mechanism comprises an electronic circuit.

10. The combination of claim 9 wherein the pulsing mechanism causes the one or more of the disinfecting radiation sources to generate a pattern of radiation across a surface of a lens stored in the storage compartment.

11. The combination of claim 1 additionally comprising a processor executing software and wherein the generated pattern of radiation is based upon instructions included in the software.

12. The combination of claim 6 wherein the light emitting diodes emit between about 50 microwatts and 5 watts of power.

13. The combination of claim 7 wherein disinfecting radiation source is capable of emitting radiation in a wavelength of between 250 nanometers and 280 nanometers.

14. The combination of claim 1 wherein the disinfecting radiation emitted by one or both of the germicidal bulbs comprises a sufficient intensity and length of time of exposure to a storage compartment proximate to the base to kill an organism on an ophthalmic lens stored in the storage compartment.

15. The combination of claim 11 wherein the processor can be used for controlling the generation of disinfecting radiation.

16. The combination of claim 15 wherein a time period that a disinfecting radiation is provided the disinfecting radiation source is based upon a logical control signal generated by the processor.

17. The combination of claim 15 wherein intensity at which a disinfecting radiation is provided is based upon a logical control signal generated by the processor.

18. The combination of claim 11 additionally comprising an audio component operative to provide an audio signal based upon operation of the source of disinfecting radiation.

19. The combination of claim 11 additionally comprising a feedback loop system for measuring the disinfecting radiation after it passes through the diffusing material.

20. The combination of claim 19 additionally comprising one or more sensors positioned in proximity with the diffusing material capable of detecting an intensity value for the feedback loop system.

21. The combination of claim 11 additionally comprising a display for displaying a status of a disinfecting process based upon digital data transmitted by the processor.

22. The combination of claim 11 additionally comprising a digital storage for storing information related to a disinfecting process.

23. The combination of claim 1 wherein the vibration generation device comprises a piezoelectric mechanism.

24. The combination of claim 1 wherein the piezoelectric mechanism is operated based upon a logical signal generated by a processor.

25. The combination of claim 11 additionally comprising a universal serial bus connector for providing logical communication between one and both of: the processor and the digital storage; and personal processing device.

26. The combination of claim 11 additionally comprising a universal serial bus connector for providing an electrical current for operating the storage base.

27. The combination of claim 1 additionally comprising an electrical storage for storing power to operate the storage base.

28. The combination of claim 27 wherein the electrical storage comprises one or more rechargeable batteries.

29. The combination of claim 27 wherein the electrical storage comprises one or more lithium ion batteries.

30. The combination of claim 7 wherein the ophthalmic lens storage compartment comprises an alignment artifact for aligning a contact lens to receive disinfecting radiation emitted by one or more of the germicidal bulbs and the light emitting diodes at an angle essentially orthogonal to a plane across a perimeter edge of the contact lens.

31. The combination of claim 7 wherein the ophthalmic lens storage compartment comprises a storage case transparent to ultraviolet radiation and ultraviolet radiation emitted by a germicidal bulb is direct at an angle essentially orthogonal to a plane across one or both of a bottom and a top of the storage case.

32. The combination of claim 4 wherein the ophthalmic lens storage compartment additionally comprises a magnet and the base additionally comprises a source of magnetic pulses, wherein the magnetic pulses vibrate the ophthalmic lens storage compartment.

\* \* \* \* \*